(12) United States Patent
Inkrott et al.

(10) Patent No.: US 6,894,194 B2
(45) Date of Patent: May 17, 2005

(54) PRODUCTION OF DITHIODIGLYCOL

(75) Inventors: Kenneth E. Inkrott, Spring, TX (US); Michael S. Matson, Bartlesville, OK (US); Alex Pauwels, Antwerp (BE)

(73) Assignee: Chevron Phillips Chemical Company, The Woodlands, TX (US)

( * ) Notice: Subject to any disclaimer, the term of this patent is extended or adjusted under 35 U.S.C. 154(b) by 0 days.

(21) Appl. No.: 10/728,769

(22) Filed: Dec. 8, 2003

(65) Prior Publication Data

US 2004/0116748 A1 Jun. 17, 2004

Related U.S. Application Data

(62) Division of application No. 10/306,703, filed on Nov. 27, 2002, now abandoned.

(51) Int. Cl.$^7$ .................... C07C 321/00; C07C 323/00; C07C 381/00
(52) U.S. Cl. .................... 568/22; 568/18; 568/20; 568/21; 568/61; 568/62; 568/63
(58) Field of Search .................... 568/22, 21, 18, 568/20, 61, 62, 63, 26, 25, 23

(56) References Cited

U.S. PATENT DOCUMENTS

| 3,299,146 A | 1/1967 | Gillette et al. |
| 3,755,461 A | 8/1973 | Kvasnikoff et al. |
| 4,067,901 A | 1/1978 | Gladstone et al. |
| 4,721,813 A | 1/1988 | Mark et al. |
| 4,937,385 A | 6/1990 | Buchholz et al. |
| 5,001,269 A | 3/1991 | Gongora et al. |
| 5,026,915 A | 6/1991 | Buchholz et al. |
| 5,068,445 A | 11/1991 | Arretz |
| 5,312,993 A | 5/1994 | Arretz |

FOREIGN PATENT DOCUMENTS

EP  1 081 134 A1  3/2001

OTHER PUBLICATIONS

CPCHem, *Material safety data sheet for di0(2–hydroxyethyl) disulfide* (May 21, 2001) (CAS#1892–29–1).

Primary Examiner—Elvis O. Price
(74) Attorney, Agent, or Firm—McDermott Will & Emery LLP

(57) ABSTRACT

In a process to make dithiodiglycol by oxidation of β-mercaptoethanol with sulfur, an improved product is recovered when a 1–10 mol % excess of β-mercaptoethanol is used and hydrogen sulfide is removed by vacuum or nitrogen sparge. A typical product contains 88.1 mol % (92.0 wt %) dithiodiglycol, 2.3 mol % (2.9 wt %) trithiodiglycol and 9.6 mol % (5.1 wt %) unreacted β-mercaptoethanol. Reaction of this product with 35 to 50 wt % solution hydrogen peroxide reduces residual β-mercaptoethanol to less than 0.02 wt % mercaptan. Residual water of about 3.6 wt % after hydrogen peroxide treatment is reduced to less than 1 wt % by vacuum stripping and/or nitrogen sparge or with a wiped film evaporator.

24 Claims, 1 Drawing Sheet

PRODUCTION OF DITHIODIGLYCOL

This application is a divisional of application Ser. No. 10/306,703 filed Nov. 27, 2002 now abandoned.

FIELD OF THE INVENTION

The invention relates to a preparing a sulfur-containing compound by reacting a thiol or mercaptan, and particularly to a process for the production of dithiodiglycol.

BACKGROUND OF THE INVENTION

Dithiodiglycol (otherwise referred to as DIHEDS, di-hydroxyethyl disulfide, 2,2'-dithiodiethanol or DTDG) is a well-known article of commerce, being used as a chemical intermediate in the manufacture of many useful compounds, such as lubricant additives.

In general, disulfides can be produced by the oxidation of the corresponding mercaptan with an oxidizing agent, such as sulfur or oxygen. Most alkyl disulfides have low to negligible water solubility. For the production of these alkyl disulfides, removal of water is a simple matter of phase separation of the water from the disulfide. However, dithiodiglycol is miscible with water.

In the production of dithiodiglycol, excess β-mercaptoethanol (otherwise referred to as BME or 2-mercaptoethanol) is frequently used to increase the production of disulfides as compared to trisulfides. The excess β-mercaptoethanol at the end of the reaction has proven to be particularly difficult to remove by any single physical means, including vacuum stripping or wiped film evaporation. Distillation of dithiodiglycol as an overhead-product is difficult, because it has a boiling point of 163° C. at 3 torr. Prolonged heating of dithiodiglycol can produce decomposition and significant discoloration of the material.

There is a need in the art for an improved method of making dithiodiglycol with low residual β-mercaptoethanol, low residual water, and low alkyl trisulfide content.

SUMMARY OF THE INVENTION

The invention provides a method for making an alkyl disulfide. The method of the invention includes a combination of chemical and physical separation steps to achieve the desirable grade of alkyl disulfide. The invention provides a low cost and safe oxidation process, avoiding both the safety concern of using oxygen for oxidation and the cost concern of using hydrogen peroxide for the entire oxidation. The invention provides a high quality alkyl disulfide product, by using excess mercaptan to make a product low in trisulfide (a "heavies" impurity). The invention further provides for removal of excess mercaptans (a "lights" impurity) with only small amounts of peroxide. The combination of mercaptan oxidation with peroxide results in a more desirable intermediate product, with no by-products other than water. The invention further provides for water removal by the use of either vacuum or nitrogen gas stripping or a device such as a wiped film evaporator, falling film evaporator or other thin-film evaporator. The time needed for this water removal step is shortened, because this step only requires the removal of small amounts of water.

In one embodiment, the alkyl disulfide is dithiodiglycol. In this embodiment, the method involves the oxidation of β-mercaptoethanol with sulfur. An improved beginning product is recovered when a 1–10 mol % excess of β-mercaptoethanol is used and when residual hydrogen sulfide is removed by vacuum or nitrogen sparge. Reaction of this beginning product with hydrogen peroxide quantitatively converts β-mercaptoethanol to product dithiodiglycol and reduces residual β-mercaptoethanol to less than 0.02 wt % mercaptan. This peroxide step not only results in more efficient product formation but also reduces odor as a result of the process. Residual water after hydrogen peroxide treatment (for example, about 4 wt %±2 wt %, or about 3.6 wt %) is reduced to less than 1 wt %. The residual water can be removed, for example, by vacuum stripping, by vacuum stripping with nitrogen sparge, or in a wiped film evaporator, falling film evaporator or other thin film evaporator.

DETAILED DESCRIPTION OF THE INVENTION

Figure 1:
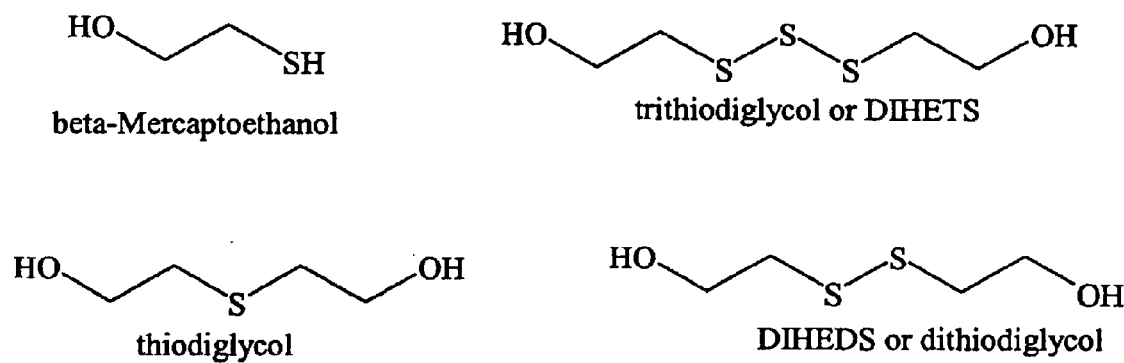
FIG. 1 is a diagram of the structures of several relevant molecules. DIHETS or dihydroxyethyltrisulfide is the same molecule as trithiodiglycol.

The invention provides a method for making an alkyl disulfide with sulfur, by first oxidizing a mercaptan with sulfur. A 1–10 mol % excess of mercaptan is used. Hydrogen sulfide is removed from the product by vacuum or nitrogen sparge. In one embodiment, most of the hydrogen sulfide evolved during this reaction (e.g., greater than 90%, such as 90–95%, of the hydrogen sulfide) is then recovered. (As used herein, the term "greater than" is understood to mean "greater than or equal to" and the term "less than" is understood to mean "less than or equal to", unless a contrary meaning is indicated.) In this embodiment, most of the remaining hydrogen sulfide is removed in subsequent steps, such as by nitrogen sparge or vacuum stripping.

While any mercaptan can be used for making a disulfide, one of skill in the art will appreciate that the method is advantageous for those reactions where it is not possible to separate the desired disulfide product from the mercaptan and "heavies" by distillation. Some mercaptans in this regard are $C_2$ to $C_{20}$ alkyl mercaptans, cycloalkylmercaptans, and other functionalized mercaptans such as 3-mercaptopropionate (acid and esters).

In one embodiment, the alkyl disulfide is dithiodiglycol. In this embodiment, the mercaptan is β-mercaptoethanol. In a particular embodiment, the invention provides a dithiodiglycol product having a minimum of 95% purity for dithiodiglycol (or a minimum of 98% dithiodiglycol plus trithiodiglycol), 1% maximum water content, and less than 0.1% β-mercaptoethanol.

When sulfur is used as the oxidant in the method of the invention and β-mercaptoethanol as the mercaptan, a series of equilibrium reactions are established, as shown below:

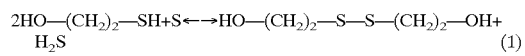
$$2HO-(CH_2)_2-SH+S \leftrightarrow HO-(CH_2)_2-S-S-(CH_2)_2-OH+H_2S \quad (1)$$

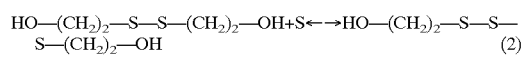
$$HO-(CH_2)_2-S-S-(CH_2)_2-OH+S \leftrightarrow HO-(CH_2)_2-S-S-S-(CH_2)_2-OH \quad (2)$$

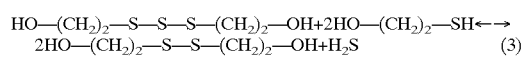
$$HO-(CH_2)_2-S-S-S-(CH_2)_2-OH+2HO-(CH_2)_2-SH \leftrightarrow 2HO-(CH_2)_2-S-S-(CH_2)_2-OH+H_2S \quad (3)$$

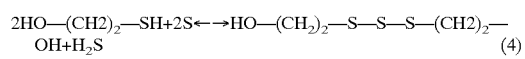
$$2HO-(CH2)_2-SH+2S \leftrightarrow HO-(CH_2)_2-S-S-S-(CH2)_2-OH+H_2S \quad (4)$$

The use of sulfur as an oxidant in reaction (1) has been useful. As the reaction progresses, hydrogen sulfide is evolved and removed to shift the equilibrium to the right side of the equation. Unfortunately, if the stoichiometry is exactly two moles of β-mercaptoethanol per mole of sulfur, the equilibrium reaction will ultimately produce an intermediate product, in a reasonable reaction time, that still contains about 10 mol % β-mercaptoethanol and 5 mol % of the trisulfide (e.g., reaction (2)). By the method of the invention, however, using a small (1 to 10 mol %) excess of β-mercaptoethanol and removing the resulting hydrogen sulfide by either vacuum or nitrogen sparge, we have produced a typical intermediate product with a distribution of approximately 88.1 mol % dithiodiglycol (92.0 wt %) (range of 90 wt %±3 wt %), 2.3 mol % trisulfide (2.9 wt %) (range of 3 wt %±2 wt %) and 9.6 mol % unreacted β-mercaptoethanol (5.1 wt %) (range of 5 wt %±2 wt %). It is believed that excess β-mercaptoethanol and stripping of hydrogen sulfide shifts the equilibrium of reaction (3).

Guidance for methods using these equilibrium reactions is provided in U.S. Pat. Nos. 3,299,146; 3,755,461; 4,721,813; 4,937,385; 5,001,269; 5,026,915; 5,068,445 and 5,312,993, each incorporated herein by reference. Prior methods of producing dithiodiglycol have not all used the three reactions described above. For example, U.S. Pat. No. 4,721,813 discloses a different method for the preparation of the compound of the invention. Moreover, U.S. Pat. No. 4,937,385 discloses contact of an alkyl mercaptan with elemental sulfur to form a dialkyl disulfide, using both a catalyst and a molar excess of elemental sulfur; that process does not use hydroxyalkene or hydroxymercaptan. By contrast, the process of the invention can use a catalyst, such as amines (triethylamine) or caustic (sodium hydroxide).

Additional information on dithiodiglycol is provided under CAS# 1892-29-1. The melting point for anhydrous dithiodiglycol is 25° C. Water containing dithiodiglycol freezes at much lower temperature. The boiling point is 163° C. at 3 torr.

During the initial hydrogen sulfide production, greater than 80% of the hydrogen sulfide, (for example, greater than 90% of the hydrogen sulfide, such as greater than 99% of the hydrogen sulfide) can be removed. In one embodiment, the hydrogen sulfide that is removed is recovered for use. This recovery can be by methods known to those of skill in the art, such as by condensation. When hydrogen sulfide evolution slows on its own, use of the nitrogen sparge or vacuum stripping can be started to help remove from solution as much of the residual hydrogen sulfide as possible as a way to push the equilibrium to dithiodiglycol.

In contrast to the method of the invention, the production of dithiodiglycol via an oxygen oxidation would produce a product with low β-mercaptoethanol, but the product would have a water content of at least 10.5 wt %. This is a substantial amount of water to remove, and thus is a costly process. Oxidation of β-mercaptoethanol with hydrogen peroxide would produce a crude product with at least 30% water if 50% peroxide solution were used. Accordingly, the use of sulfur is useful, because the produced hydrogen sulfide by-product can be recovered for use. Also sulfur is a less hazardous oxidant than oxygen or hydrogen peroxide.

Following these reactions, the residual β-mercaptoethanol is next reacted with hydrogen peroxide. In one embodiment, the hydrogen peroxide is a 27.5 wt % to 70 wt % solution. In another embodiment, the hydrogen peroxide is a 27.5 wt % to 50 wt %. We have used a hydrogen peroxide solution of about 35 wt % for safety reasons, although up to 70 wt % can be obtained and used safely with the correct cautionary procedures and equipment. The higher the peroxide concentration, the lower the amount of water that will need to be removed by the stripping process. Thus, one of the advantages of the method of the invention is that the amount of water to remove after complete oxidation of the mercaptan is much less. On other embodiments of the invention, the residual β-mercaptoethanol is removed by other oxidants, such as oxygen, sulfur or organic peroxides.

The production of dithiodiglycol is an equilibrium reaction. That means that there will always be some unreacted β-mercaptoethanol present as well as the trisulfide. Typically, the crude product will contain about 90–94% dithiodiglycol, about 3–5% trisulfide and 3–5% β-mercaptoethanol. The use of the peroxide (such as hydrogen peroxide, which converts β-mercaptoethanol to additional dithiodiglycol) reduces the residual β-mercaptoethanol to <0.02 wt % mercaptan.

Next is the removal of the residual water to <1 wt %. The peroxide-treated crude product contains very low β-mercaptoethanol, <0.1%, but also contains water. The water is present from the reaction as well as from the water that was introduced with the 30% peroxide solution. The peroxide-treated crude product contains from 8–10% water, about 2.5–3% trisulfide with the remainder being product dithiodiglycol. Moreover, treatment done to remove the water should not result in any coloration of the product.

In one embodiment, residual water is removed by using a wiped film evaporator, falling film evaporator or other thin film evaporator. Water content can be reduced effectively in a batch reactor by vacuum stripping with some stirring and nitrogen sparging through the solution, while heating to about 60–80° C. at 50 to 100 torr. Nitrogen sparge rates are typically controlled at a moderate level. At 50 torr, the lower temperature can be used. A faster flow rate at the higher temperature gives similar results. Using a wiped film evaporator, the water content can be easily reduced from about 7% to about 0.5%.

As used herein, the term "nitrogen sparge" refers to the fact that nitrogen vapors are introduced into the liquid phase of the crude product, so that water or hydrogen sulfide can vaporize and be swept out the reactor. Typically, the residual hydrogen sulfide vapors are swept to a flare line.

In another embodiment, residual water is removed by using a vacuum strip (for example, with a nitrogen sparge) from a vessel. Mixing in the vessel can aid in the removal of residual water.

The details of one or more embodiments of the invention are set forth in the accompanying description above. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The following EXAMPLES are presented in order to more fully illustrate embodiments of the invention. These examples should in no way be construed as limiting the scope of the invention, as defined by the appended claims.

EXAMPLE 1

Production of Crude DIHEDS Product

TABLE I provides some process data from a DIHEDS production. For the production, 5 weight parts of β-mercaptoethanol are reacted with 1 weight part sulfur in the presence of triethylamine (TEA) catalyst (0.06 wt % of β-mercaptoethanol amount). After $H_2S$ removal and recovery, the remaining β-mercaptoethanol is reacted with $H_2O_2$ (35%). The relative amount of $H_2O_2$ needed to react with the β-mercaptoethanol is calculated as follows:

kg $H_2O_2$ (35%)=(mass in reactor)×(wt % β-mercaptoethanol/100)× 0.623.

Thus, the amount of hydrogen peroxide used equals about 15 kg $H_2O_2$ (35%) per 1000 ppm SH (0.24 wt % β-mercaptoethanol).

After the hydrogen peroxide addition, the product contains about 5 wt % water. Results are shown in TABLE I below. Sample 1 of each batch is the results after hydrogen sulfide stripping. The other samples are β-mercaptoethanol oxidation products after various hydrogen peroxide additions.

TABLE 1

DITHIODIGLYCOL PRODUCTION

| Batch/Sample | 'Lights" wt % | β-mercapto-ethanol wt % | Dithiodiglycol wt % | Trithiodiglycol wt % | "Heavies" wt % | $H_2O$ wt % |
|---|---|---|---|---|---|---|
| Batch 1 | | | | | | |
| 1 | 0.22 | 5.34 | 91.72 | 2.49 | 0.23 | |
| 2 | 0.21 | 0.01 | 97.15 | 2.43 | 0.2 | 4.8 |
| Batch 2 | | | | | | |
| 1 | 0.22 | 5.07 | 92.08 | 2.39 | 0.24 | |
| 2 | 0.27 | 0.01 | 97.36 | 2.17 | 0.19 | 4.7 |
| Batch 3 | | | | | | |
| 1 | 0.29 | 5.61 | 90.65 | 3.22 | 0.23 | |
| 2 | 0.28 | 0.02 | 96.38 | 3.15 | 0.17 | 5 |
| Batch 4 | | | | | | |
| 1 | 0.15 | 6.19 | 90.28 | 3.14 | 0.24 | |
| 2 | 0.15 | 0.02 | 96.64 | 3 | 0.19 | 5.1 |
| Batch 5 | | | | | | |
| 1 | 0.29 | 5.8 | 90.64 | 3.02 | 0.25 | |
| 5 | 0.26 | 0.02 | 96.68 | 2.86 | 0.18 | 5 |
| Batch 6 | | | | | | |
| 1 | 0.07 | 5.85 | 90.72 | 3.12 | 0.24 | |
| 4 | 0.11 | 0.02 | 96.57 | 3.1 | 0.2 | 4.8 |
| Batch 7 | | | | | | |
| 1 | 0.15 | 6.04 | 90.45 | 3.14 | 0.22 | |
| 5 | 0.12 | 0.01 | 96.55 | 3.14 | 0.18 | 5.3 |
| Batch 8 | | | | | | |
| 1 | 0.28 | 4.82 | 90.74 | 3.9 | 0.26 | |
| 5 | 0.24 | 0.02 | 95.65 | 3.88 | 0.21 | 4.6 |
| Batch 9 | | | | | | |
| 1 | 0.23 | 5.17 | 90.51 | 3.82 | 0.27 | |
| 2 | 0.27 | 0.02 | 95.84 | 3.71 | 0.16 | 4.5 |
| Batch 10 | | | | | | |
| 1 | 0.15 | 5.52 | 90.9 | 3.11 | 0.32 | gel |
| 2 | 0.14 | <0.01 | 96.59 | 3.1 | 0.17 | 4.8 |
| Batch 11 | | | | | | |
| 1 | 0.18 | 3.79 | 91.82 | 4 | 0.21 | |
| 2 | 0.17 | <0.01 | 95.57 | 4.1 | 0.16 | 3.8 |
| Batch 12 | | | | | | |
| 1 | 0.21 | 5.72 | 90.44 | 3.45 | 0.18 | |
| 2 | 0.2 | <0.01 | 96.65 | 3.04 | 0.11 | 4.6 |
| Batch 13 | | | | | | |
| 1 | 0.35 | 6.76 | 89.34 | 3.35 | 0.2 | |
| 2 | 0.13 | 0.02 | 96.47 | 3.24 | 0.14 | 5.2 |

EXAMPLE 2

Vacuum Stripping of Residual Water from Dithiodiglycol

This EXAMPLE shows the removal of the residual water from wet dithiodiglycol to <1 wt % by vacuum stripping. The water-containing samples of dithiodiglycol, some of which we treated with hydrogen peroxide, contained about 3–5% water and 3% of the trisulfide.

Several runs were performed in the 1-liter autoclave under vacuum and simultaneous nitrogen sparging. The nitrogen was sparged into the liquid through a dip tube fitted with a metal frit. Some of the results are summarized in TABLE 2 below:

TABLE 2

BATCH REACTOR STRIPPING

| Run # | Vacuum (torr) | Temp. (° C.) | Time (hrs) | Nitrogen flow | % Water |
|---|---|---|---|---|---|
| 1 | 10 | 50 | 6.0 | none | 0.92 |
| 2 | 100 | 50 | 6.0 | none | 3.54 |
| 3 | 50–100 | 80 | 7.0 | 2.4 L/min | 0.13* |
| 4 | 450–475 | 80 | 6.0 | 2.4 L/min | 0.09* |
| 5 | 200 | 50 | 6.0 | 0.3 L/min | 1.91 |
| 6 | 100 | 60 | 6.0 | 0.3 L/min | 0.37 |
| 7 | 10 | 50 | 9.0 | none | 0.98 |

1-liter autoclave used with stirrer on at 200 rpm, dithiodiglycol contained 4.8% water
*Some dithiodiglycol was also removed from the reactor due to the high nitrogen sparge rate In one run at 200 torr and 50° C. and a sparge rate of 285 cc nitrogen per minute, the water content was reduced to 1.9% in 6 hours. E.g., Run #5 in TABLE 2. Another run at 100 torr and 60° C. and 285 cc/minute resulted in 0.4% water in 6 hours. E.g., Run #6 in TABLE 2.

Some additional runs were done with a much higher nitrogen flow rate (not measured but in excess of 2 liter/minute). In these runs, the water was down to about 0.1%, but about 8–12% of the dithiodiglycol was lost overhead with the water because of foaming. E.g. Runs #3 and #4 in TABLE 2.

There was not a significant reduction in water content in 5 hours at 50 to 100 torr and 50 to 80° C. range with only stirring and no nitrogen sparge. E.g., Run #3 in TABLE 2.

If the vacuum was lowered to 10 torr, then the water content could be reduced to the desired level at 50° C. in about six to seven hours. E.g., Run #1 in TABLE 2.

In a 1-gallon reactor, the stripping took nine hours at 10 torr and 50° C. E.g., Run #7 in TABLE 2.

In another run, Run #8, not shown in TABLE 2, in a 1-liter autoclave with mechanical stirrer at 200 rpm, there was no reduction in water content in six hours at 50 torr and 80° C. When the pressure was lowered to 10 torr, water content was reduced from 3.6% to 1.2% in 9 hours.

In another run, Run #9, not shown in TABLE 2, the starting material had not undergone any hydrogen peroxide treatment. This run was performed in the 1-liter autoclave at 50° C. and 10 torr. There was no impact on the β-mercaptoethanol level. The test began with about a 5.1% water content, which remained unchanged after six hours.

In general, the tests with nitrogen sparging in addition to the stirring indicated that the water content could be reduced to <1% at 100 torr at 60° C. in six hours at a sparge rate of 285 cc nitrogen per minute.

EXAMPLE 3

Vacuum Stripping of Residual Water from Dithiodiglycol

In one pilot plant water stripping assay, wet dithiodiglycol was charged to 100-gallon reactor. The results are shown below in TABLE 3.

TABLE 3

PILOT PLANT STRIPPING

| Run # | Vacuum (torr) | Temp. (° C.) | N₂ Sparge (lbs/hr) | Agitation | Time (hrs) | % Water (initial) | % Water (final) |
|---|---|---|---|---|---|---|---|
| 1 | 80 | 80 | 4.7 | On | 2.0 | 5.2 | 0.05 |
| 3 | 200 | 80 | 3.9 | On | 10.5 | 5.4 | 0.3 |
| 6 | 100 | 80 | 0.0 | Off | 9.3 | 6.3 | 3.6 |

570 lbs. dithiodiglycol charged to 100 gallon reactor

In another pilot plant water stripping assay, wet dithiodiglycol was charged to 30-gallon reactor. Water was stripped from the dithiodiglycol with a batch time of about 2.5 hours at 100 torr and 80° C., with or without nitrogen sparge, but with full agitation.

EXAMPLE 4

Stripping of Residual Water by Wiped Film Evaporator

This EXAMPLE shows the removal of the residual water to <1 wt % in a wiped film evaporator.

A glass vertical hanging wiped film evaporator was used in the tests. The evaporator has a diameter of about 5 cm and the heated zone is about 17 cm long, giving a heated surface of about 267 square centimeters (about 43 square inches). The evaporator is heated using an external heating mantle. The temperature is monitored between the mantle and glass surface. 500 grams material (3.6% water) were charged to the vessel. The wall of the vessel was heated to the desired temperature while the system was put under the desired vacuum. The flow of dithiodiglycol was adjusted to try to maintain a constant temperature on the walls.

Typically, it took 2.6 to 5 hours to pass 500 grams of product through the evaporator. At 100 and a skin temperature of 90° C. and 2.6 hour total time, the water content in the 500 grams of product was reduced to 0.5% residual water. At 50 torr, 65° C. and 5 hours, the water content was lowered to 0.81%. A test at 50 torr and 105° C. resulted in water content of 0.52% in a 4.0-hour run time. Reducing the vacuum to 25 torr at 105° C. resulted in a water content of 0.42% in a run time of 3.5 hours.

Some of the results are summarized in TABLE 4 below:

TABLE 4

WIPED FILM EVAPORATOR WATER STRIPPING

| Run # | Vacuum (torr) | Temp. (° C.) | Time (hrs) | % Water |
|---|---|---|---|---|
| 1 | 50 | 65–70 | 5.0 | 0.81 |
| 2 | 50 | 105–115 | 4.3 | 0.52 |
| 3 | 24 | 107–119 | 3.5 | 0.42 |
| 4 | 100 | 85–95 | 2.7 | 0.49 |

500 grams of water containing dithiodiglycol (3.6% water) was charged to wiped film evaporator vessel. The outside wall of wiped film evaporator glass body was heated using electric heating mantle.

There was no significant change in color during these tests. For comparison, in a regular distillation, at temperatures of >80° C. for prolonged times, the color could darken. The higher the temperature and the longer the time, the darker the material becomes. Distillation of dithiodiglycol to take the product overhead in a glass column resulted in a very dark kettle product, but a pale yellow product was taken overhead.

In another test, the wiped film evaporator was run at about 100–120° C. and around 10 torr. We were able to reduce the β-mercaptoethanol from 5% level down to a lower level.

EXAMPLE 5

Summary of Commercial Scale Wiped Film Evaporator Assays

A commercial scale water stripping of wet dithiodiglycol was performed using a wiped film evaporator. The dithiodiglycol was water stripped from the starting 5.2% water to average final content of 0.9% water with some fractions at low levels.

An analysis of the final product is shown in TABLE 5.

TABLE 5

ANALYSIS OF DITHIODIGLYCOL FINAL PRODUCT SAMPLE

| Properties | Units | Target | Actual |
|---|---|---|---|
| Appearance | APHA | clear liquid | clear liquid |
| Color | | 200 max | 150 |
| Mercaptan Sulfur | wt % | <0.05 | 0.002 |
| Acid Number | mg KOH/g | <2.5 | 0.18 |
| Water Content | wt % | <1.0 | 0.63 |
| GC Analysis | | | |
| Lights | | 0.1–0.4 | 0.3 |
| DIHEDS | | 95.0–97.0 | 96.1 |
| DIHETS | | 1.0–3.5 | 3.2 |
| Heavies | | 0.2–0.5 | 0.4 |

The foregoing description has been presented only for the purposes of illustration and is not intended to limit the invention to the precise form disclosed, but by the claims appended hereto.

What is claimed is:

1. A method for making a disulfide, comprising the steps of:
   (1) oxidation of a mercaptan with sulfur, wherein the oxidation reaction has a 1–10% molar excess of mercaptan to sulfur;
   (2) removing hydrogen sulfide;
   (3) reacting the product of step (2) remaining after the hydrogen sulfide removal with hydrogen peroxide; and
   (4) removing water to less than 1 wt %.

2. The method of claim 1, wherein the mercaptan is β-mercaptoethanol and the disulfide is dithiodiglycol.

3. The method of claim 1, wherein the mercaptan is selected from the group consisting of $C_2$ to $C_{20}$ alkyl mercaptans, cycloalkylmercaptans, functionalized mercaptans and acids and esters thereof.

4. The method of claim 1, wherein the oxidation reaction has a 3–5% molar excess of mercaptan to sulfur.

5. The method of claim 1, wherein the water is removed to less than 0.5 wt %.

6. The method of claim 1, wherein greater than 80% of the hydrogen sulfide is removed.

7. The method of claim 6, wherein greater than 90% of the hydrogen sulfide is removed.

8. The method of claim 1, wherein the removal of the hydrogen sulfide is by vacuum, nitrogen sparge or a combination thereof.

9. The method of claim 1, wherein the hydrogen peroxide in step (3) has a concentration of hydrogen peroxide in solution of between 5 wt % and 98 wt %.

10. The method of claim 1, wherein the hydrogen peroxide in step (3) has a concentration of hydrogen peroxide in solution of between 25 wt % and 70 wt %.

11. The method of claim 1, wherein the hydrogen peroxide in step (3) has a concentration of hydrogen peroxide in solution of between 27.5 wt % and 50 wt %.

12. The method of claim 1, wherein the water removal in step (4) is by vacuum stripping.

13. The method of claim 1, wherein the water removal in step (4) is by vacuum stripping with a nitrogen sparge.

14. The method of claim 1, wherein the water removal in step (4) is by a wiped film evaporator.

15. The method of claim 2, wherein the product of step (2) comprises greater than 92 wt % dithiodiglycol.

16. The method of claim 2, wherein the product of step (2) comprises less than 3 wt % trithiodiglycol.

17. The method of claim 2, wherein the product of step (2) comprises less than 5 wt % unreacted β-mercaptoethanol.

18. The method of claim 2, the oxidation reaction has a 3–5% molar excess of mercaptan to sulfur.

19. The method of claim 2, wherein the removal of the hydrogen sulfide is by vacuum, nitrogen sparge or a combination thereof.

20. The method of claim 2, wherein greater than 80% of the hydrogen sulfide is removed.

21. The method of claim 20, wherein greater than 90% of the hydrogen sulfide is removed.

22. The method of claim 2, wherein the residual water is less than 0.5 wt %.

23. The method of claim 2, the product of step (2) comprises greater than 87 wt % dithiodiglycol; less than 5 wt % trithiodiglycol; and less than 7 wt % unreacted β-mercaptoethanol.

24. The method of claim 1, wherein the residual β-mercaptoethanol in the product of step (3) is less than 0.02 wt % mercaptan.

* * * * *